United States Patent [19]

Minachev et al.

[11] 4,131,750

[45] Dec. 26, 1978

[54] PROCESS FOR THE PRODUCTION OF FATTY ALCOHOLS

[76] Inventors: Khabib M. Minachev, Leninsky prospekt, 57, kv. 15; Evgeny S. Mortikov, Leninsky prospekt, 61/1, kv. 34, both of, Moscow; Alexandr S. Leontiev, ulitsa Gagarina, 13, kv. 13, Bashkirskaya ASSR, Salavat; Anatoly G. Smirnov, Leningradsky prospekt, 78, korpus 5, kv. 110, Moscow; Nikolai F. Kononov, ulitsa Garibaldi, 13/54, kv. 4, Moscow; Alexei A. Masloboev-Shvedov, Nagatinskaya naberezhnaya, 16, kv. 75, Moscow; Alexandr K. Zhomov, ulitsa Tsjurjupy, 16, korpus 2, kv. 70, Moscow; Nikolai I. Kholdyakov, ulitsa Marshala Birjuzova, 2, kv. 23, Moscow, all of U.S.S.R.

[21] Appl. No.: 488,183

[22] Filed: Jul. 12, 1974

[51] Int. Cl.² ............................................. C07C 29/04
[52] U.S. Cl. .................................. 568/901; 252/416; 252/468
[58] Field of Search ........................ 260/641; 568/901

[56] References Cited

U.S. PATENT DOCUMENTS

| 3,173,855 | 3/1965 | Miale et al. | 260/641 |
| 3,257,469 | 6/1966 | Kovach | 260/641 |
| 3,459,815 | 8/1969 | Noddings et al. | 260/641 |
| 3,493,518 | 2/1970 | Jonassen et al. | 260/641 |

OTHER PUBLICATIONS

Kirk–Othmer, "Ion Exchange," Encyclopedia of Chemical Technology, vol. 3, pp. 344–345.

*Primary Examiner*—Joseph E. Evans
*Attorney, Agent, or Firm*—Fleit & Jacobson

[57] ABSTRACT

A process for the production of fatty alcohols containing from 2 to 5 carbon atoms, which comprises reacting an olefin containing from 2 to 5 carbon atoms with water. The reaction is effected at a temperature of from 150 to 280° C and a pressure of from 10 to 70 atmospheres in the presence of an aluminosilicate catalyst, type Y zeolite, containing a calcium cation and chromium oxide, and which may also contain a chromium cation and/or at least one cation of a rare-earth element. The process of the invention is preferably carried out in a mutual solvent for the reactants (the olefin and water), and under a mild set of conditions and provides for a sufficiently high yield of the desired product. The high selectivity of the catalyst employed in the process ensures a high purity of the product alcohols. The catalyst is further distinguished by its stability.

11 Claims, No Drawings

PROCESS FOR THE PRODUCTION OF FATTY ALCOHOLS

The present invention relates to processes for the production of fatty alcohols containing 2 to 5 carbon atoms which are employed in the chemical industry, e.g., as solvents, extracting agents and intermediate products in the manufacture of dyestuffs, rubbers and elastics.

There exist several processes for the production of fatty alcohols, including those which contain 2 to 5 carbon atoms, by reacting olefins with water in the presence of catalysts.

Thus, for example, it is known in the art to produce fatty alcohols by reacting olefins with water at a temperature of 300° C. and a pressure of 70 atm. in the presence of the phosphoric acid-on-kieselguhr catalyst. According to this prior technique, 4.2 to 21.1 percent of the olefin is converted to alcohol The disadvantages of this process are as follows: the acid attacks the material of the apparatus; the catalyst consumption rates are quite high; in the course of the process, fresh phosphoric acid has to be continuously added; the process temperature is high; and a number of difficulty separable byproducts are formed, such as aldehydes, esters and condensation products.

Another known process for the production of fatty alcohols is also available.

This latter process comprises charging a reactor with a catalyst, amorphous aluminoscilicate, and passing therethrough a mixture of steam and olefins at a temperature of 150 to 260° and a pressure of 100 to 500 atm. The level of conversion of the olefins to alcohols reaches 30 percent at a weight alcohol content in the catalyst of 2.5 percent.

The disadvantages of said latter process consist in the need to maintain a high pressure, which in turn calls for specialty apparatus and high-pressure compressors, as well as the low yield of the desired product. Besides, under the conditions selected, the process likewise gives rise to byproducts which are difficult to separate, such as aldehydes, esters, etc.

It is an object of the present invention to provide a process for the production of fatty alcohols containing 2 to 5 carbon atoms, such as would ensure a sufficiently high yield of the desired product.

It is another object of the present invention to provide a simplified process as compared with the prior art techniques.

Accordingly, there is provided a process for the production of fatty alcohols containing 2 to 5 carbon atoms, which comprises reacting an olefin containing 2 to 5 carbon atoms with water at a temperature of 150 to 280° C. and at elevated pressure in the presence of an aluminosilicate catalyst. In accordance with the invention, the process is effected at a pressure of 10 to 70 atmospheres, and the catalyst is type Y zeolite containing a calcium cation as well as at least one of the following three components (1) a chromium cation; (2) cations of rare-earth elements; and (3) chromium oxide.

Of all the possible compositions of the aluminosilicate catalyst the following are recommended to be employed in the proposed process:

(1) type Y zeolite containing cations of calcium, chromium and rare-earth elements;

(2) type Y zeolite containing a calcium cation and chromium oxide;

(3) type Y zeolite containing cations of calcium, chromium and reare-earth elements and chromium oxide;

(4) type Y zeolite containing calcium and chromium cations; and (5) type Y zeolite containing cations of calcium and rare-earth elements.

The reaction of olefins with water, i.e. hydration of olefins, is known to be an acid reaction and as such catalyzable by sulfuric, phosphoric and hydrofluoric acids.

Type Y zeolite containing cations of rare-earth elements is sufficiently active in this reaction, for its acidity is close to that of sulfuric acid and far higher than that of the above-mentioned amorphous aluminosilicates or phosphoric acid. However, with their branched surface, considerable electrostatic field and tendency to intensively adsorb polar substances (water), zeolites, tend to adsorb water preferentially so that the surface of the catalyst is largely covered with water which prevents adsorption of the second component, viz, the olefin. Therefore, if type Y zeolite containing cations of rare-earth elements is employed in the process as the catalyst, the hydration reaction is preferably carried out under more rigorous conditions. Thus, the rare-earth constituent of the catalyst may be of the following desirable composition: cerium, 64%; lanthanum, 23%; samarium, 10%; praseodymium, 2%; other rare-earth elements, 1%. Concentrates of rare-earth elements of other compositions can also be used.

Chromium, introduced into the catalyst both as an oxide and as a cation, promotes preferential adsorption of olefins. It is a commonly known fact that the heat of adsorption of olefins on chromium is higher than on other elements. Hence, the hydration reaction rate on zeolites containing chromium in any form is far higher than on chromium-free zeolites, particularly at low temperatures and pressures.

The calcium cation, apart from providing active (acid) centers, also stabilizes the cations of rare-earth elements and chromium over the areas of the zeolite surface accessible to the olefins and water.

Thus, all the above-mentioned components (cations of calcium and rare-earth elements and, particularly, chromium cation and chromium oxide) of the catalyst promote olefin and water reaction on the catalyst, thereby providing for a higher yield of the desired product at comparatively low pressure values.

The reaction of olefin and water is preferably effected in the presence of an organic substance capable of dissolving both the olefin and water.

Such an organic substance in which both the olefin and water can be dissolved improves the water-olefin contact, thereby adding to the reaction rate.

Such an organic substance may be acetone, one of fatty alcohols or cellulose.

As compared with the prior art technique wherein the catalyst is represented by amorphous aluminosilicate, the process of the present invention can be carried out under milder conditions, viz, at a pressure of 10 to 70 atm instead of 100 to 500 atm. The yield of fatty alcohols rises to 56 percent, whereas the concentration of fatty alcohol rises to 22 percent, which makes the task of its recovery much easier.

The mild conditions of the process and the high selectivity of the catalyst combine to provide for a high purity of the desired product, which is practically free from any impurities of aldehydes, ketones, esters, condensation products, etc.

The considerable area of the catalyst surface and its high thermal stability are conducive to its stability in service. After 40 hours of continuous service without reactivation the catalyst showed no signs of degeneration in activity or selectivity. Should the catalyst get clogged with coke, its properties are completely restored by oxidative reactivation at 500 to 600° C. After 4 months of service in a synthesis-reactivation mode, the catalyst lost none of its activity; furthermore, the rate of its consumption is for practical purposes nil.

The catalyst is quite cheap since it is prepared from inexpensive concentrates of rare-earth elements, type Y zeolite as well as commercially produced chromium and calcium salts.

The proposed process requires no corrosion-proof apparatus and produces no harmful pollution emissions.

The process of this invention is carried out as follows.

An isothermal or adiabatic reactor is charged with the catalyst. Said catalyst is purged with nitrogen at a temperature of 300 to 500° C. for 30 minutes and then cooled in a stream of nitrogen down to the reaction temperature (150 to 280° C.). Then the reactor is charged with the feedstock — a liquid mixture of water and an olefin or an elefin-containing fraction — at a pressure of 10 to 70 atmospheres.

The molar ratio of water to olefin may be varied from 1:1 to 10:1. The space velocity of feedstock delivery may range from 0.5 to 5.0 $hr^{-1}$, preferably 2.0 $hr^{-1}$. In order to raise the yield of the product alcohol as well as its concentration in the catalyst, it is preferred that organic solvents capable of dissolving both water and the olefins should be added to the feedstock prior to charging. The molar ratio of water to solvent in the feedstock may vary from 1:10 to 10:1, preferably from 1:0.5 to 1:1. Upon completion of the reaction, the desired product is recovered in a pure form by any known technique, e.g. by rectification.

Should the catalyst get clogged with coke, which may occur after a long time of service (at least 50 hours), the catalyst is subjected to oxidative reactivation by purging it with a mixture of air and nitrogen for 5 hours. Multiple reactivation (over 15 times) was found to affect in no way the initial activity of the catalyst.

Practice of the novel process of this invention will be further understood from the following specific examples.

EXAMPLE 1

Powder-like Na-Y type zeolite with a molar ratio of $SiO_2$: $Al_2O_3$ = 4.6 is mixed with a binder, aluminum hydroxide, taken at the rate of 30 percent of the zeolite weight in terms of dry substance. The resultant mixture is extruded into cylindrical granules measuring 4 by 5 mm which are subjected to drying at a temperature of 100 to 170° C. and then roasting in a stream of nitrogen at a temperature of 500 to 550° C. After cooling, the granules are successively treated at 20° C. with aqueous solutions of calcium chlorides and of rare-earth elements of a 5–10 percent cerium concentrate (3 equivalents of calcium and rare-earth elements per 1 equivalent of sodium in the zeolite). The cerium concentrate contains, wt.%:cerium, 54.7; lanthanum, 24.5; neodymium, 14.8; praseodymium, 4.4. Then the granules are washed with distilled water to a negative reaction to chlorine ions and roasted in a stream of nitrogen at a temperature of 500 to 550° C. for 6 hours. On cooling, the granules are treated with a 5-percent aqueous solution of chromium nitrate (taken in the ratio of 3 equivalents of chromium per 1 equivalent of sodium in the initial zeolite) for 2 hours at 60° C. Then the catalyst is washed with distilled water and dried in a stream of nitrogen at a temperature of 100 to 200° C.

As a result, the level of exchange for calcium is 20 percent of the theoretical; for rare-earth elements 41 percent of the theoretical; and for chromium 12 percent of the theoretical.

The product catalyst amounting to 50 cu.cm. (35 g) is loaded into an isothermal flow reactor 1 m in length and 20 mm in inner diameter. The upper portion of the reactor packed with porcelain pellets serves for the preheating of the feedstock. A mixture of water and a butane-butylene fraction containing up to 40 percent by weight of butenes is passed through the reactor at a temperature of 200° C., a pressure of 50 atm and a space velocity of 2 $hr^{-1}$. In the starting mixture the molar ratio of water to butenes is 6:1.

The yield of butyl alochols is 45 to 54 percent by weight; their concentration in the catalyst is 20 to 22 percent.

EXAMPLE 2

Powder-like type Ca-Y zeolite with a molar ratio of $SiO_2$: $Al_2O_3$ = 4.7 and a level of exchange for calcium of 85 percent of the theoretical is mixed with aluminum hydroxide and chromium hydroxide taken at the respective rates of 10 and 20 percent of the zeolite weight in terms of dry substance. The resultant mixture is extruded into cylindrical granules measuring 4 by 5 mm which are dried in a stream of nitrogen at a temperature of 100 to 200° C. to give a catalyst containing 20 percent by weight of chromium oxide.

The catalyst thus obtained to the extent of 50 cu.cm. (35 g) is loaded into a reactor such as the one described in Example 1. A mixture of water and butenes taken at the molar ratio of 6 water to 1 butenes is passed through the reactor at a temperature of 200° C., a pressure of 60 atm and a space velocity of 1.5 $hr^{-1}$.

The yield of butyl alcohols is 42 to 46 percent by weight; their concentration in the catalyst is 17 to 18%.

EXAMPLE 3

Powder-like type Na-Y zeolite with a molar ratio of $SiO_2$:$Al_2O_3$ = 4.7 is successively treated at 20° C. with aqueous chloride solutions of calcium and rare-earth elements of a 5–10 percent lanthanum concentrate (3 equivalents of calcium and rare-earth elements per 1 equivalent of sodium in the zeolite). The lanthanum concentrate contains, wt.%: lanthanum, 62.5; neodymium, 15; cerium, 2.5. After the exchange reaction is over, the powder is washed with distilled water on a filter to a negative reaction to chlorine ions, mixed with aluminum hydroxide and chromium hydroxide taken at the respective rates of 20 and 10 percent of the zeolite weight in terms of dry substance, and extruded into cylindrical granules measuring 4 by 5 mm which are subjected to drying in a stream of nitrogen at a temperature of 100 to 200° C.

The dried granules are treated for 2 hours at 60° C. with a 5-percent aqueous solution of chromium nitrate taken at the rate of 3 equivalents of chromium per 1 equivalent of sodium in the starting zeolite. Then the catalyst is washed with distilled water and dried in a stream of nitrogen at a temperature of 100 to 200° C.

The level of exchange for calcium is 50 percent of the theoretical; for rare-earth elements 20 percent of the theoretical; for chromium 10 percent of the theoretical.

The resultant catalyst comprises 10 percent by weight of chromium oxide.

The catalyst amounting to 50 cu.cm. (35 g) is loaded into a reactor of the type described in Example 1. A mixture of water and isopentene in the molar ratio of 8 water to 1 isopentene is passed through the reactor at a temperature of 150° C. a pressure of 60 atm and a space velocity of 2 hr$^{-1}$.

The yield of isoamyl alcohol is 47 to 51 percent by weight; its concentration in the catalyst is 18 to 20%.

EXAMPLE 4

6 by 5 mm granules of type Ca-Y zeolite, granulated without a binder, with a molar ratio of $SiO_2:Al_2O_3 = 3.9$ and having a level of exchange for calcium of 85 percent of the theoretical are treated for 2 hours at 60° C. with a 5-percent aqueous solution of chromium nitrate taken at the rate of 3 equivalents of chromium per 1 equivalent of calcium in the starting zeolite. Then the catalyst is washed with distilled water and dried in a stream of nitrogen at a temperature of 100 to 200° C. In the resultant catalyst, the level of exchange for calcium is 65 percent of the theoretical; for chromium 20 percent of the theoretical.

The catalyst amounting to 50 cum.cm. (35 g) is loaded into a reactor of the type described in Example 1.

A mixture of water and propylene, taken in the molar ratio of 9 water to 1 propylene is passed through the reactor at a temperature of 200° C., a pressure of 70 atm and a space velocity of 2 hr$^{-1}$.

The yield of isopropyl alcohol is 50 percent by weight; its concentration in the catalyst is 17 percent.

EXAMPLE 5

A reactor of the type described in Example 1 is charged with a catalyst of the type described in Example 3.

A mixture of water, acetone and butenes, taken in the molar ratio of 6 water to 0.5 acetone to 1 butenes, is passed through the reactor at a temperature of 150° C., a pressure of 30 atm. and a space velocity of 1 hr$^{-1}$.

The yield of butyl alcohols is 36 to 39 percent by weight; their concentration in the catalyst is 17 to 18 percent (after elimination of the acetone by rectification).

A pressure reduction to 10 atm. reduces the yield of alcohols to 25 to 30 percent by weight and their concentration in the catalyst to 11 or 14 percent.

EXAMPLE 6

Na-Y zeolite in the form of granules measuring 5 by 10 mm of a molar ratio of $SiO_2:Al_2O_3 = 3.6$ is treated at a temperature of 70° C. with a 5-percent aqueous solution of calcium chloride taken at the rate of 5 equivalents of calcium per 1 equivalent of sodium. On completion of the exchange reaction, the granules are washed with distilled water to a negative reaction to chlorine ions and roasted in a stream of nitrogen at a temperature of 400 to 500° C. for 6 hours. After cooling, the granules are treated with 5-percent aqueous chloride solutions of rare-earth elements of a cerium concentrate and ammonium at 70° C. for 2 hours. The cerium concentrate contains, wt.%; cerium, 64; lanthanum, 23; samarium, 10; praseodymium, 2.

Then the catalyst is washed with distilled water, dried in a stream of nitrogen at a temperature of 100 to 200° C., and roasted at a temperature of 500 to 550° C. for 6 hours. As a result, the level of exchange for calcium is 25 to 35 percent of the theoretical; for rare-earth elements 30 to 37 percent of the theoretical.

The catalyst amounting to 100 cu.cm. (65g) is loaded into a reactor of the type described in Example 1. A mixture of water and ethylene in the molar ratio of 3 water to 1 ethylene is passed through the reactor at a temperature of 280° C., a pressure of 70 atm. and a space velocity of 1 hr$^{-1}$.

The yield of ethyl alcohol is 6 to 8 percent.

Capillary chromatography shows no byproducts, such as aldehydes, ketones, esters, etc., in the reaction products.

A mixture of water and butene in the molar ratio of 6 water to 1 butene is passed through the same catalyst specimen at a temperature of 150° C., a pressure of 60 atm. and a space velocity of 1 hr$^{-1}$.

The yield of butyl alcohol is 25 to 30 percent; the concentration of the alcohol in the catalyst is at least 10%.

A temperature rise to 200° C. has no effect on the alcohol yield. A rise in the molar ratio of the reagents to 9 water to 1 butene brings about a rise in the butyl alcohol yield to 40 percent.

What is claimed is:

1. A process for the production of fatty alcohols containing from 2 to 5 carbon atoms, comprising reacting an olefin containing from 2 to 5 carbon atoms with water at a temperature of from 150° C. to 280° C. and a pressure of from 10 to 70 atmospheres in the presence of a catalyst of an aluminosilicate Y-type zeolite containing a calcium cation and chromium oxide.

2. The process of claim 1 where the catalyst additionally contains a chromium cation.

3. The process of claim 1 wherein the catalyst additionally contains a chromium cation and at least one cation of a rare-earth element.

4. The process of claim 1 wherein the olefin is a butene.

5. The process of claim 1 wherein the olefin is isopentene.

6. The process of claim 1 wherein the olefin is propylene.

7. The process of claim 1 wherein the olefin is ethylene.

8. The process of claim 1 wherein the water and the olefin are present in a molar ratio ranging from 1:1 to 10:1, respectively.

9. The process of claim 1 wherein the reaction between the olefin and the water is conducted in a mutual solvent for these reactants.

10. The process of claim 9 wherein the water and the mutual solvent are present in a molar ratio ranging from 1:10 to 10:1, respectively.

11. The process of claim 9 wherein the mutual solvent is acetone.

* * * * *